(12) United States Patent
Pritchard

(10) Patent No.: US 7,144,721 B1
(45) Date of Patent: Dec. 5, 2006

(54) TREATMENT OF WOUNDS

(75) Inventor: David Idris Pritchard, University Park (GB)

(73) Assignee: The Secretary of the State of Defense, Defence Science and Technology Laboratory of Porton Down, Salisbury (GB)

(*) Notice: Subject to any disclaimer, the term of this patent is extended or adjusted under 35 U.S.C. 154(b) by 312 days.

(21) Appl. No.: 10/111,252

(22) PCT Filed: Oct. 20, 2000

(86) PCT No.: PCT/GB00/04034

§ 371 (c)(1),
(2), (4) Date: Aug. 23, 2002

(87) PCT Pub. No.: WO01/31033

PCT Pub. Date: May 3, 2001

(30) Foreign Application Priority Data

Oct. 22, 1999 (GB) ................................. 9925005.2

(51) Int. Cl.
*C12N 9/64* (2006.01)
*C07K 1/00* (2006.01)

(52) U.S. Cl. .......................................... 435/226; 530/14
(58) Field of Classification Search ................ 435/212; 424/78.06, 94.64
See application file for complete search history.

(56) References Cited

U.S. PATENT DOCUMENTS 5,688,768 A    11/1997  Coughlin et al.

FOREIGN PATENT DOCUMENTS

| WO | WO 87 07907 A | 12/1987 |
|---|---|---|
| WO | WO 88 03151 A | 5/1988 |
| WO | WO-98/18456 | 5/1998 |
| WO | WO-99/43809 | 9/1999 |

OTHER PUBLICATIONS

Massova et al Matrix metalloproteinases: structures, evolution, and diversification. FASEB J. Sep. 1998;12(12):1075-95. Review.*
Witkowski et al, Conversion of a beta-ketoacyl synthase to a malonyl decarboxylase by replacement of the active-site cysteine with glutamine. Biochemisty. Sep. 7, 1999;38(36):11643-50.*
Wishart et al, A single mutation converts a novel phosphotyrosine binding domain into a dual-specificity phosphatase. J Biol Chem. Nov. 10, 1995;270(45):26782-5.*
Basu et al, Serine proteinase from rice bean. Indian J Biochem Biophys. Dec. 1996;33(6):491-7.*
Jany et al, Trypsin-like endopeptidases from the midguts of the larvae from the hornets of *Vespa orientalis* and *Vespa crabro*. Insect Biochem. 1978 8(4): 221-223 and 225-230.*
Steadman's Medical Dictionary 26th Edition 1995, p. 1964.*
Zhu et al, Stabilization of proteins encapsulated in injectable poly (lactide- co-glycolide) Nat Biotechnol. Jan. 2000;18(1):52-7.*
Yager et al, The proteolytic environment of chronic wounds. Wound Repair Regen. Nov.-Dec. 1999;7(6):433-41. Review.*
Mirastschijski et al, Ectopic localization of matrix metalloproteinase-9 in chronic cutaneous wounds. Hum Pathol. Mar. 2002;33(3):355-64.*
Kumar et al., Purification and characterization of a thermostable alkaline protease from alkalophilic *Bacillus pumilus*. Lett Appl Microbiol. 2002;34(1):13-7.*
McDonagh et al., Production of caseinophosphopeptides (CPPs) from sodium caseinate using a range of commercial protease preparations. International Dairy Journal (1998), 8(1), 39-45.*
Bowles M.V. et al.: "Characterization of Proteolytic and Collagenolytic Enzymes from the Larvae of *Lucilia-cuprina* the Sheep Blowfly," *Australian Journal of Biological Sciences*, vol. 41, No. 2, 1988, pp. 269-278.
Constable S.A.: "A Comparison of Proteases Produced by Larvae of *Lucilia cuprina* (Wiedemann), *L. sericata* (Meigen, *Calliphora augur* (F.) and *C. stygia* (F.) (Diptera: Calliphoridae)," *Journal of Australian Entomological Society*, vol. 33, No. 3, 1994, pp. 203-210.
Sandeman R. M. et al.: "Tryptic and Chymotryptic Proteases Released by Larvae of the Blowfly *Lucilia-cuprina*,"*International Journal for Parasitology*, vol. 20, No. 8, 1990, pp. 1019-1024.
Young Anna R. et al.: "Characterization of ES Products Involved in Wound Initiation by *Lucilia cuprina* Larvae," *International Journal for Parasitology*, vol. 26, No. 3, 1996, pp. 245-252.
Database Biosis (online), Biosciences Information Service, Philadelphia, PA, US; 1997; Mumcuoglu K Y et al.: "Maggot Therapy for Gangrene and Osteomyelitis", vol. 132, No. 5, 1997, pp. 323-325, 384.
Blackhart et al. "Ligand Cross-reactivity within the Protease-activated Receptor Family" *Journal of Biological Chemistry*, vol. 271, No. 28, 1996, pp. 16466-16471, XP-002323721.
Nystedt et al. "Molecular Cloning and Functional Expression of the Gene Encoding the Human Proteinase-activated Receptor 2" *European Journal of Biochemistry*, vol. 232, No. 1, 1995, pp. 84-89, XP-002323722.
Database Geneseq [Online] "Human protease-activated receptor 3 (PAR3) agonist peptide" Oct. 12, 1998, XP-002323724.

* cited by examiner

*Primary Examiner*—Sheridan L. Swope
(74) *Attorney, Agent, or Firm*—Edwards Angell Palmer & Dodge LLP; Peter C. Lauro, Esq.

(57) ABSTRACT

An isolated protein, for use in treatment of wounds, is characterized in that it is secreted by the organism *Lucilia sericata* and it exhibits proteolytic activity against FITC-casein at a pH of 8.0 to 8.5. The protein exhibits proteolytic activity against Tosyl-Gly-Pro-Arg-AMC but not against Suc-Ala-Ala-Phe-AMC, and its proteolytic activity against FITC-casein and Tosyl-Gly-Pro-Arg-AMC is inhibited by the serine proteinase inhibitors PMSF and AMPSF. The protein is also bound by immobilized aminobenzamidine.

3 Claims, 5 Drawing Sheets

Lane 1 Standard (Sigma 7B
Lane 3 Aminobenzamidine eluate (Peak II)
Lane 5 Start
Lane 6 Flow through (Peak I)

TREATMENT OF WOUNDS

This application is a U.S. national phase application, filed pursuant to 35 U.S.C. §371, of PCT international application no. GB00/04034, filed on Oct. 20, 2000, which was published in English on May 3, 2001 under international publication no. WO 01/31033 A2 and which claims priority to GB 9925005.2, filed Oct. 22, 1999.

TECHNICAL FIELD

The present invention relates to the treatment of wounds More particularly, it relates to substances which promote the healing of wounds, to compositions and to dressings which incorporate such substances and to a method of treating wounds using such substances.

BACKGROUND TO THE INVENTION

Efficient wound healing is a complex physiological process which involves many mechanisms including cell migration, growth factor secretion, angiogenesis, tissue remodelling and the intrinsic proteinase/antiproteinase balance of the wound contributing in concert and in an apparently staged manner to accelerate controlled tissue regeneration.

Wound care products are essential in modern medical practice, especially for the treatment of patients with chronic wounds or burns. Many different substances have previously been proposed as having activities which contribute to the healing of wounds. These previously proposed substances include streptokinase, collagenase and streptodomase (all obtained from bacterial sources), bromelain (from pineapples), plasmin and trypsin (obtained from cattle) and krill enzymes (obtained from crustacea). Clinical trial data indicate that such substances are only partially effective in promoting the healing of wounds.

The larvae (maggots) of the green bottle fly, *Lucilia sericata*, are known to have significant wound healing attributes as live organisms. Debridement treatment using the larvae of *Lucilia sericata*, has become a widely accepted clinical practice. However, little has been reported in the literature about the way in which these larvae go about their task of cleaning wounds to an extent that conventionally untreatable wounds heal.

Although efficacious, live larvae are unpleasant to many patients and the use of live larvae on wounds and the introduction of their crude secretions into wounds, which inevitably occurs when the larvae are used, are unacceptable to many patients and to many medical practitioners. The use of live organisms also increases the risk of infection or allergic reactions in the patient.

It is an object of the invention to overcome at least some of the above problems.

SUMMARY OF THE INVENTION

We have now purified an enzyme which occurs naturally in the crude secretions of the larvae of *Lucilia sericata*, and which exhibits trysin-like serine proteinase activity and wound-healing promotion activity. The use of the purified enzyme in the treatment of a wound avoids the need to bring live organisms and/or their crude secretions into contact with the wound.

The present invention provides an isolated protein characterised in that:
 i) it is secreted by the organism *Lucilia sericata*;
 ii) it exhibits optimum proteolytic activity against FITC-casein at a pH of 8.0 to 8.5;
 iii) it exhibits proteolytic activity against Tosyl-Gly-Pro-Arg-AMC but not against Suc-Ala-Ala-Phe-AMC;
 iv) its proteolytic activity against FITC-casein and Tosyl-Gly-Pro-Arg-AMC is inhibited by the serine proteinase inhibitors PMSF and APMSF; and
 v) it is bound by immobilised aminobenzamidine.

The invention also provides an isolated protein, characterised in that it is a functional homologue of the protein of the invention. Typically the protein will be a naturally produced protein secreted by an insect in its larval stage. Suitable insect are envisaged as being those that are used in their larval form in the treatment of wounds. It is also envisaged that clones of either the *Lucilia* protein, or functional homologues thereof, will form part of the invention and may be used in wound treatment. In this regard, the protein of the invention may be expressed in bulk in an active recombinant form in an insect/baculovirus expression system.

In a further aspect, the invention relates to a method for treating a wound to promote healing thereof in a human or non-human mammal which comprises applying to the wound a therapeutically effective amount of a sterile composition comprising a protein according to the invention as active ingredient. The invention also relates to the use of a protein of the invention in the preparation or manufacture of a medicament for the treatment of wounds.

In a further aspect, the invention relates to an isolated peptide selected from the group consisting of; Ser-Phe-Leu-Leu-Arg-Asn (SEQ ID NO: 1); Ser-Leu-Ile-Gly-Lys-Val (SEQ ID NO: 2); Thr-Phe-Arg-Gly-Ala-Pro (SEQ ID NO: 3); Gly-Tyr-Pro-Gly-Gln-Val (SEQ ID NO: 4), and a peptide having an N-terminal sequence selected from: Ser-Phe-Leu-Leu-Arg-Asn (SEQ ID NO: 1); Ser-Leu-Ile-Gly-Lys-Val (SEQ ID NO: 2); Thr-Phe-Arg-Gly-Ala-Pro (SEQ ID NO: 3); or Gly-Tyr-Pro-Gly-Gln-Val (SEQ ID NO: 4), or a protected analogue thereof which is protected against aminopeptidase activity, and to the use of one or more of such peptides in a method for treating a wound to promote healing thereof in a human or non-human mammal which comprises applying to the wound one or more of said peptides. Furthermore, the invention relates to the use of such a peptide in the preparation or manufacture of a medicament for the treatment of wounds.

In one embodiment of the invention, there is provided a dressing for a wound, which comprises a sterile support carrying a therapeutically effective amount of a protein and/or at least one peptide according to the invention. Where the words "comprises" and "comprising" are used herein, it is intended that these may have the meanings "includes" and "including", respectively, to the extent that other procedures or other materials are not excluded.

DETAILED DESCRIPTION OF THE INVENTION

Figure 1:
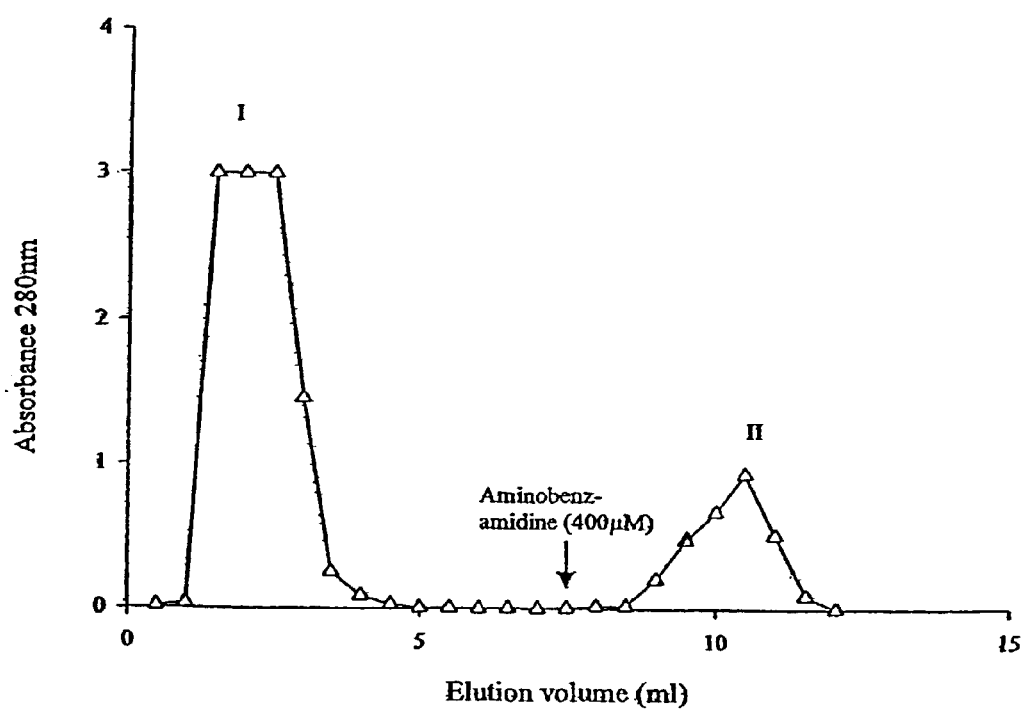
FIG. 1 is an elution profile of *Lucilia sericata* excretory/secretory (ES) having been passed through an affinity column.

The protein of the present invention exists, in nature, in the excretory/secretory (ES) secretions of the larvae of *Lucilia sericata*.

The larval ES secretions demonstrate a classical pH optimum of 8.0–8.5 when hydrolysing the fluorescent protein substrate fluorescein isothiocyanate-casein (FITC-casein). By pre-incubating the larval ES secretions, prior to monitoring the hydrolysis of FITC-casein, with the irreversible low molecular weight inhibitors 4-(amidinophenyl) methane sulphonyl fluoride (APMSF; an inhibitor for all trypsin-like serine proteases but not chymotrypsin-like serine proteinases) or with phenyl methanesulphonyl fluoride (PMSF; an inhibitor for all serine proteinases) it is shown that larval ES secretions have two types of serine proteinase activity; a trypsin-like activity and a chymotrypsin-like activity. The dual activity is confirmed by monitoring the hydrolysis of the fluorescent peptide substrates Tosyl-Gly-Pro-Arg-AMC (selective for trypsin-like proteinases) and Suc-Ala-Ala-Pro-Phe-AMC (SEQ ID NO: 5) (selective for chymotrypsin-like proteinases), in which "AMC" represents 7-amino-4-methyl coumarin and "Suc" represents succinyl.

In addition to the predominant serine proteinase activity detected in the ES secretions of *Lucilia sericata* other less predominant activity is present. The presence of an aspartyl and metalloproteinase activity has been detected though no cysteinyl activity is shown. The aspartyl activity, shown by monitoring FITC-casein hydrolysis, is pronounced at pH 5.0 and is successfully inhibited by the class specific inhibitor pepstatin A. The metalloproteinase activity present is demonstrated by the ability of the ES secretions to hydrolyse a leucine aminopeptide, revealing the presence of an exopeptidase. Exopeptidases recognise free —$NH_2$ aminoacids in peptides Leucine aminopeptide hydrolysis by *Lucilia sericata* ES is only inhibited by the $Zn^{2+}$ chelator 1,10-phenanthroline, a classic metalloproteinsase inhibitor. This inhibition reflects the presence of an exopeptidase with a metalloproteinase enzymic nature.

The ES secretions have an α-amylase activity calculated to be about 0.88 units/liter. Additionally, phosphatase activity (hydrolysis of orthophosphoric monoester bond) is present in the larval ES secretions although this activity is approximately 50 times lower when compared to the proteinases. Lipase activity (hydrolysis of ester bonds found in fatty acid esters) is also identified. This lipase activity is not detected when the ES secretions are pre-incubated with the inhibitor PMSF, indicating that this hydrolysis is due to the serine proteinase in the secretions.

It can be concluded from our investigations that the predominant class of activity in the larval ES secretions is serine proteinase activity and that there are two types of serine proteinase activity present; one derived from a chymotryptic enzyme and one derived from a tryptic enzyme.

The protein of the present invention, which relates to the tryptic enzyme, may be obtained in substantially pure form from the crude ES secretions by a chromatographic procedure. The ES secretions are collected from the larvae of *Lucilia sericata* and are subjected to affinity chromatography using immobilised aminobenzamidine. Aminobenzamidine is a reversible inhibitor of trypsin-like serine proteinases. After collection of the "flow-through" material from the chromatographic procedure, i.e., the material which is not bound by the immobilised reagent, the enzyme which has been bound by the immobilised reagent may be eluted by the addition of free aminobenzamidine and collected separately.

Inhibitor studies carried out on the unbound ("flow-through") fraction and the eluted fraction using the inhibitors APMSF and PMSF show that the unbound material has activity characteristic of chymotryptic enzymes whereas the eluted fraction is a tryptic serine proteinase.

We believe that tryptic serine proteinase, isolated from the crude larval ES secretions as described above, has the ability to initiate and promote healing events in wounds. We have found that larval ES secretions are capable of degrading the extra cellular matrix (ECM)/wound components, fibronectin, laminin and collagens I, III, IV and V. These macromolecules are found in the slough of chronic wounds and also make up the "fibrin cuffs" that are predominant in chronic ulcers. The degradation of laminin and fibronectin by larval secretions is inhibited by PMSF, but not significantly by APMSF or by the metalloproteinase inhibitor 1,10-phenanthroline.

In addition, the degradation of the different forms of collagen by the predominant serine proteinase activity indicates the presence of a collagenase. This suggests that the serine proteinase activity within larval ES secretions has the potential to degrade key wound components, a requirement for the debridement stage of healing, and is involved in preventing "fibrin cuff" formation, stimulating angiogenesis, leucocyte invasion and fibroplast proliferation. In contrast to the ECM components degraded, no degradation of fibrin itself, elastin and hyaluronic acid by ES secretions has been detected, suggesting the absence of plasmin or elastase-like proteinase or hyaluronidase.

The trypsin-like enzyme isolated from crude larval ES secretions, we believe, has the ability to activate healing processes via protease-activated receptors (PARs). PAR1, which is known to be cleaved by thrombin, trypsin and factor Xa, is present on human endothelial cells, fibroblasts, keratinocytes, platelets, monocytes and smooth muscle. PAR1 agonists promote endothelium dependent vasodilation, leading to extravasation of plasma proteins and leucocytes, to cell mitogenesis, and to the healing of inflamed and damaged tissue. The PARs have attached ligands which are cleaved proteolytically by the trypsin-like enzyme of the invention to release peptides which then act to trigger other biochemical processes involved in promoting wound healing. The arginine residue at the cleavage site of the tethered ligand of PAR1 is susceptible to the action of trypsin-like proteinases. Further details of the tethered ligands and the elucidation of their sequence is given in Am. J. Physiol. 274 (1998), c1428–c1452.

As mentioned above, PARs have tethered ligands which when cleaved by the trypsin-like serine proteinase release one or more peptides into the wound area.

Normally tethered ligands of PARs which are believed, by us, to be responsible for the activation of wound healing when released include the peptides 1 to 4 below 1. Ser-Phe-Leu-Leu-Arg-Asn (SEQ ID NO: 1);
2. Ser-Leu-Ile-Gly-Lys-Val (SEQ ID NO: 2);
3. Thr-Phe-Arg-Gly-Ala-Pro (SEQ ID NO: 3); and
4. Gly-Tyr-Pro-Gly-Gln-Val (SEQ ID NO: 4).

These four peptides are agonists of PARs 1 to 4, respectively.

We believe that wound healing is promoted by the application to the wound area of one or more of these peptides, or a protected analogue thereof which is protected against aminopeptidase activity, without the need to apply the tryptic serine proteinase to the wound.

The peptides of the invention, as described above, can be prepared synthetically and purified according to the usual routes of peptide synthesis and purification known in the art. The peptide may be protected against aminopeptidase activity to enhance activity and/or to prolong the period within which the peptide remains active in the wound area. Protection against aminopeptidase activity may, for example, be achieved by the amidation at COOH substitution in the peptide using a non-coded anomalous amino acid and/or CO—NH amide bond replacement by an isostere.

The peptides (and/or protein) of the invention may be applied to a wound to induce a profile of growth factors conducive to healing. For instance, one or more peptides, either in a pure form or in a sterile carrier, can be sprinkled over the wound area or incorporated into a carrier to be applied to the wound. For instance, the peptide (and/or protein) can be incorporated or encapsulated into a suitable material capable of delivering the peptide to a wound in a slow release or controlled release manner. An example of such a suitable material is poly(lactide-co-glycolide) or PLGA particles which may be formulated to release peptides in a controlled release manner. Alternatively, one or more peptides (and/or protein) may be incorporated into a dressing to be applied over the wound. Examples of such dressings include staged or layered dressings incorporating slow-release hydrocolloid particles containing the wound healing material or sponges containing the wound healing material optionally overlayered by conventional dressings. Hydrocolloid dressings of the type currently in use, for example those available under the trademark "Granuflex", may be modified to release the peptides to the wound.

EXPERIMENTAL METHODS

1. Isolation and Assay of the Trypsin-Like Serine Proteinase of the Invention

The trypsin-like serine proteinase was purified by affinity chromatography of *Lucilia sericata* ES on aminobenzamidine agarose. The column matrix (1 ml) was equilibrated with 20 ml of 0.025M Tris-HCl buffer pH 8.0 containing 0.5M NaCl. The crude ES (0.5 ml, 70 µg/ml protein) was diluted with an equal volume of buffer before application to the column. Fractions (0.5 ml) were collected throughout the chromatography. After washing with 6.5 times column volume of buffer to remove unbound protein, the free aminobenzamidine ligand (2 ml 400 µM) was used to elicit the elution of bound material. Absorbance readings of the fractions at 280 nm was used to establish the positions of the unbound (flow-through) and bound peaks which were then collected for assay. The elution profile is shown in FIG. 1

Figure 2:
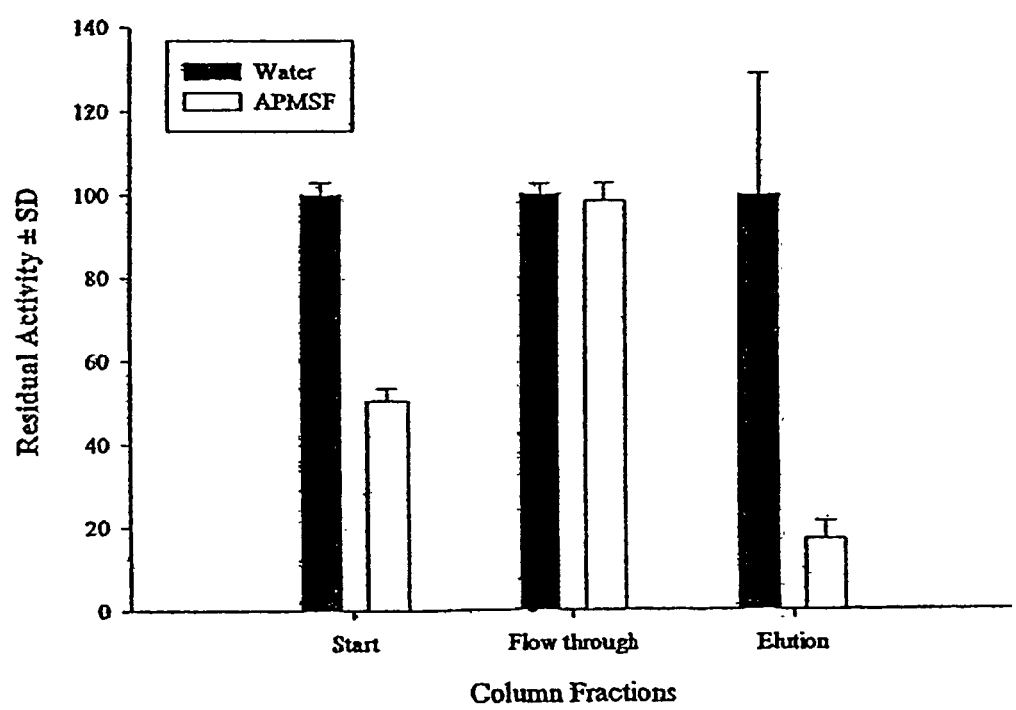
FIG. 2 shows the residual activity of the column fractions identified in FIG. 1.

Aminobenzamidine agarose binds trypsin-like serine proteinases. Following application of larval enzyme secretions to the column, unbound material passed directly through and was collected as "flow-through" (peak I). The addition of free aminobenzamidine to the column buffer elicited elution of the bound proteinase (peak II). The unbound (flow-through) material contained proteinase activity unaffected by APMSF (possibly including a a chrymotrypsin-like enzyme), whereas the activity in the aminobenzamidine elution peak was substantially abolished (80%) by APMSF, indicating purification of a trypsin-like serine proteinase activity. The residual activities of the column fractions are shown in FIG. 2.

Figure 3:
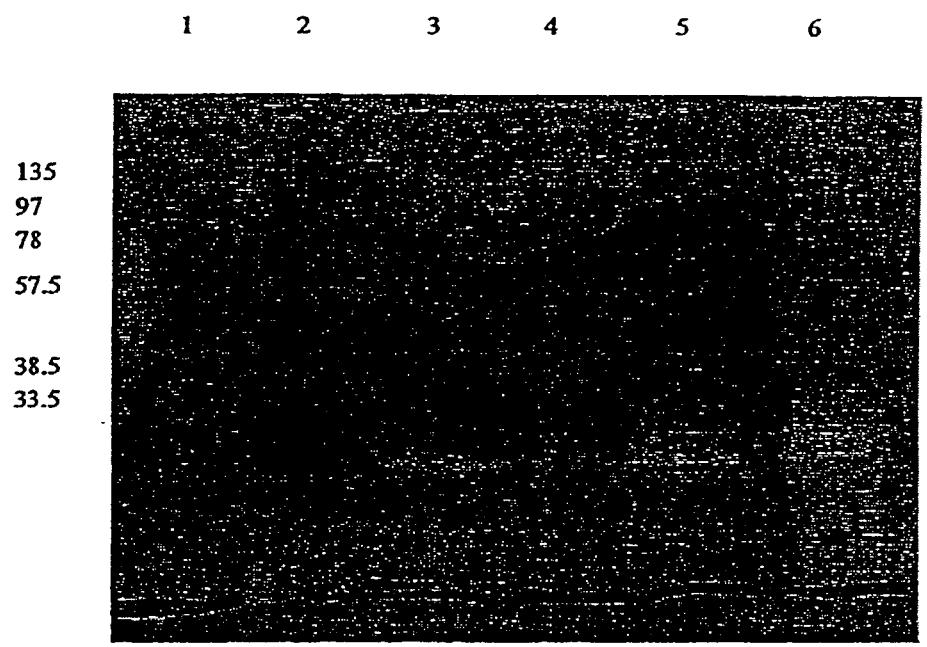
FIG. 3 shows a picture of a gel after electrophoresis of the column fractions identified in FIG. 1.

Column fractions were examined by electrophoresis in non-reducing SDS sample buffer (0.5M Tris-HCl pH 6.8 containing 4% SDS, 20% glycerol and 0.02% bromophenol blue) on 12% SDS polyacrylamide gels containing 0.1% human haemoglobin. SDS was removed by washing in 2.5% Triton X-100 (1 h) and distilled water (15 min.). Proteolysis of the haemoglobin substrate in the gel by incubation at 37° C. in 0.1M Tris-HCl buffer pH 8.0 overnight produced clear bands revealed by protein staining in Coomassie Brilliant blue corresponding to the positions of proteinase enzymes (FIG. 3). The start and flow through fractions each showed several proteinase activities however the aminobenzamidine eluted a single band. Thus the trypsin-like enzyme previously identified in the aminobenzamidine-eluted fraction (FIG. 2) was shown to have molecular weight ~25 KDa (FIG. 3).

2. Investigation of Proteolytic Behaviour of the Larval Enzyme (ES) with FITC-Casein The activity of *Lucilia sericata* ES in FITC-casein hydrolysis at pH8 was investigated using different presentations of ES (0.25 µg) as follows:
  A. ES+$H_2O$
  B. ES+ethanol
  C. ES pre-incubated with 0.2 mM PMSF
  D. ES pre-incubated with 0.6 mM PMSF
  E. ES pre-incubated with 1 mM PMSF
  F. ES pre-incubated with 0.04 mM APMSF
  G. ES pre-incubated with 0.12 mM APMSF
  H. ES pre-incubated with 0.2 mM APMSF The proteolytic activity of *Lucilia sericata* ES was inhibited following pre-incubation with the irreversible serine proteinase inhibitor PMSF. It was totally inhibited in the case where the ES had been pre-incubated with 1 mM PMSF. PMSF is dissolved in ethanol and the effect of the solvent on the activity of the ES was negligible. In contrast, approximately 50% of residual serine proteinase activity from ES was detected in the cases where the ES had been pre-incubated with the irreversible "trysin-like" specific inhibitor APMSF. Residual activity in the presence of APMSF indicates the presence of a chymotrypsin-like enzyme. The activity (%) values obtained were as follows:
  A. 100%
  B. 85.5%
  C. 13.8%
  D. 18%
  E. 0%
  F. 43.5%
  G. 47%
  H. 54%

Figure 4:
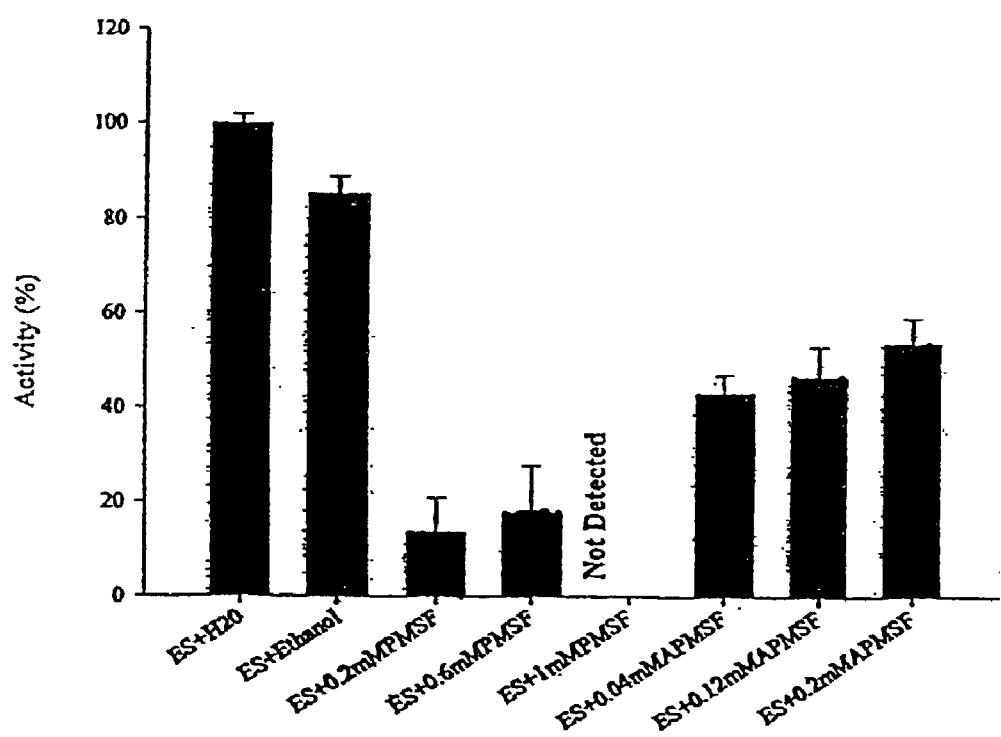
FIG. 4 shows FITC-Casein hydrolysis by *Lucilia sericata* ES in the presence of APMSF/PMSF at pH8.

These results are shown graphically in FIG. 4.

3. Investigation of the Proteolytic Activity of the Larval Enzyme (ES) Against Specific Substrates The activity of *Lucilia sericata* ES (0.25 µg) against Tosyl-Gly-Pro-Arg-AMC (a) and against Suc-Ala-Ala-Phe-AMC (b) in the presence of APMSF and PMSF was investigated using different presentations of ES as follows:
  (a)
  A. ES
  B. ES pre-incubated with 0.025 mM APMSF
  C. ES pre-incubated with 0.05 mM APMSF
  D. ES pre-incubated with 1 mM PMSF
  (b)
  E. ES
  F. ES pre-incubated with 0.2 mM APMSF
  G. ES pre-incubated with 1 mM PMSF The residual activity (%) values obtained were as follows:
  (a)
  A. 100%
  B. 14.3%

C. 3.6%
D. 0%
(b)
E. 100%
F. 86.8%
G. 1.3%

Figure 5:
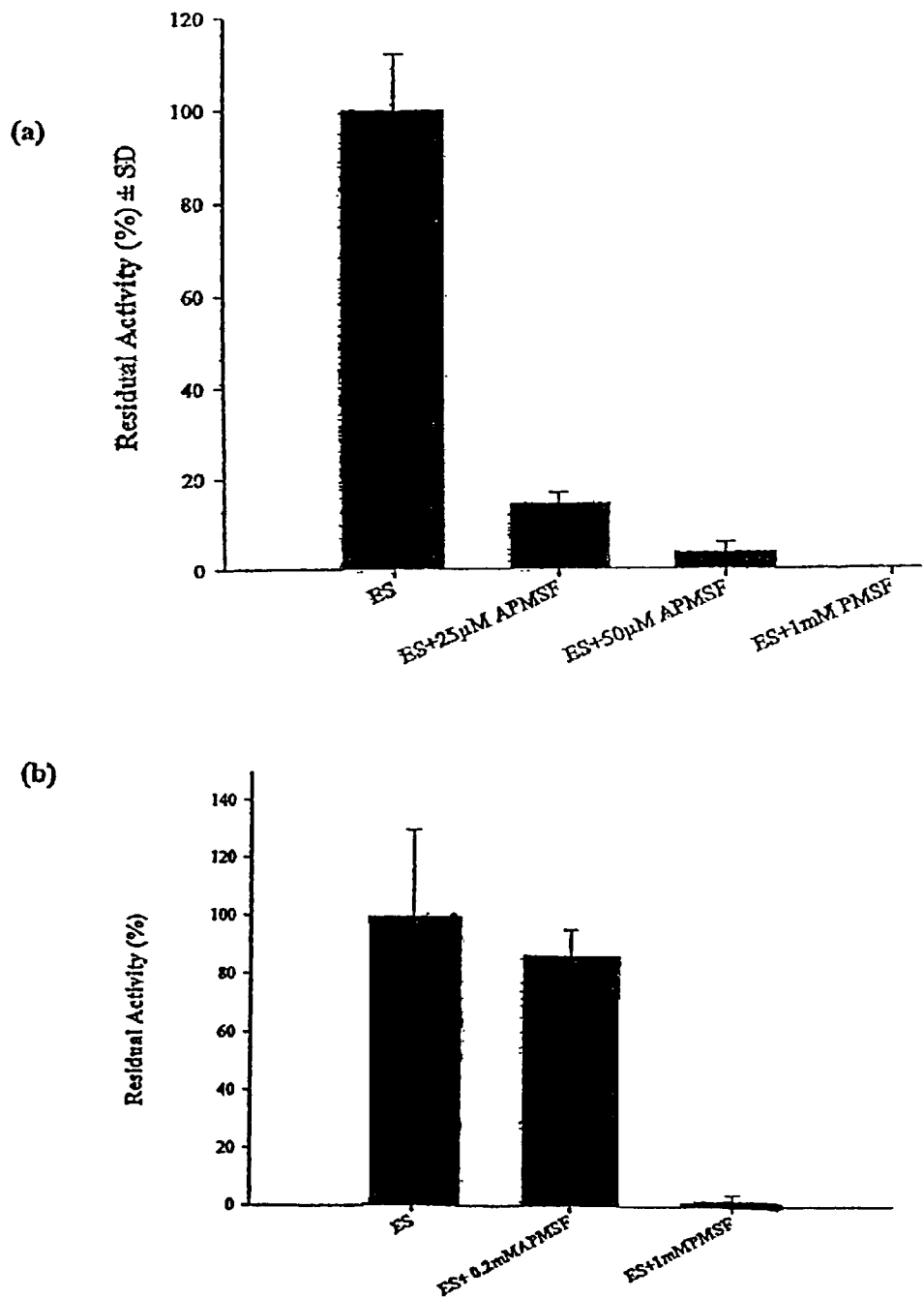
FIG. 5 demonstrates (a) Tosyl-Gly-Pro-Arg-AMC and (b) Suc-Ala-Ala-Phe-AMC hydrolysis by *Lucilia sericata* in the presence of APMSF and PMSF.

The results are shown graphically in FIG. 5.

The results for (a) reveal the "trypsin-like" serine proteinase activity present in *Lucilia sericata* ES. The hydrolysis of Tosyl-Glyc-Pro-Arg-AMC (selective for the serine proteinases thrombin and plasmin) was inhibited by 1 mM PMSF and 0.05 mM APMSF. However, the hydrolysis of the chymotryptic substrate Suc-Ala-Ala-Phe-AMC by *Lucilia sericata* ES was only inhibited by PMSF (1 mM) and not by excess APMSF (which does not inhibit chymotrypsin). The results provide further evidence of the presence in ES of two different sub-classes of serine proteinase.

As mentioned above, the invention also relates to functional homologues of the *Lucilia* protein of the invention which may be obtained from other insects having larval phases and which can potentially be used in the treatment of wounds. For example, given the teaching of the present application, it would be within the ambit of the skilled addressee, using the experimental methods disclosed herein, to assay larval secretions from other non-*Lucilia* organisms for a functional homologue of the *Lucilia* protein of the invention. Furthermore, proteinases according to the invention produced by *Lucilia* which promote wound healing may be cloned and expressed in bulk in an active recombinant form in an insect/baculovirus expression system. Genes corresponding to the proteinases will be identified by PCR or immunological screening from appropriate cDNA libraries and manipulated for expression in this system. As proteinases from diverse sources can prove difficult to express in prokaryotic expression systems, it is advantageous to use an insect expression system for the expression of the insect gene corresponding to the proteinase of the invention.

The invention is not limited to the embodiment hereinbefore described which may be varied without departing from the invention.

What is claimed is:

1. An isolated protein characterized in that:
  i) it is secreted by the organism *Lucilia sericata;*
  ii) it exhibits optimum protcolytic activity against FITC-casein at a pH of 8.0 to 8.5;
  iii) it exhibits protcolytic activity against Tosyl-Gly-Pro-Arg-AMC but not against Suc-Ala-Ala-Phe-AMC;
  iv) its proteolytic activity against FITC-casein and Tosyl-Gly-Pro-Arg-AMC is inhibited by the serine proteinase inhibitors PMSF and AMPSF; and
  v) it is bound by immobilized aminobenzamidine.

2. The isolated protein as claimed in claim 1 having a molecular weight of approximately 25 kDa.

3. The isolated protein of claim 1 which is secreted by the organism in its larval stage.

* * * * *

UNITED STATES PATENT AND TRADEMARK OFFICE
CERTIFICATE OF CORRECTION

| | |
|---|---|
| PATENT NO. | : 7,144,721 B1 |
| APPLICATION NO. | : 10/111252 |
| DATED | : December 5, 2006 |
| INVENTOR(S) | : David I. Pritchard et al. |

It is certified that error appears in the above-identified patent and that said Letters Patent is hereby corrected as shown below:

In the Title:

The Patentee respectfully requests that the title on the cover page of the patent be changed from "The Treatment of Wounds" to "Lucilia *sericata* Serine Proteinase".

In the Assignment:

The Assignee should be listed as "The Secretary of State for Defence", Defence Science and Technology Laboratory of Porton Down, Salisbury, Wiltshire, United Kingdom, SP4 0JQ (as correctly shown on the Assignment recorded in the United States Patent and Trademark Office on September 28, 2004).

In the Specification:

At column 1, line 29, "streptodomase" should read -- streptodornase --.

At column 1, line 56, "trysin" should read -- trypsin --.

At column 2, line 9, " insect" should read -- insects -- .

At column 2, line 21, "mammal" should read -- mammal, --.

At column 2, line 39, "mammal" should read -- mammal, --.

At Description of Figure 1, "(ES) having" should read -- (ES) secretions having --.

At column 3, line 36, "aminoacids" should read -- amino acids --.

At column 3, line 38, "peptides Leucine" should read -- peptides. Leucine --.

At column 4, line 13, "extra cellular" should read -- extra-cellular --.

At column 5, line 49, "was" should read -- were --.

At column 5, line 59, "a a" should read -- a --.

UNITED STATES PATENT AND TRADEMARK OFFICE
CERTIFICATE OF CORRECTION

PATENT NO. : 7,144,721 B1
APPLICATION NO. : 10/111252
DATED : December 5, 2006
INVENTOR(S) : David I. Pritchard et al.

It is certified that error appears in the above-identified patent and that said Letters Patent is hereby corrected as shown below:

At column 5, line 59, "chrymotrypsin-like" should read -- chymotrypsin-like --.

At column 6, line 36, "trysin-like" should read -- trypsin-like --.

In the Claims:

In column 9, line 29, "protcolytic" should read -- proteolytic - - .

In column 9, line 31, "protcolytic" should read -- proteolytic --.

In column 9, line 35, "AMPSF" should read -- APMSF --.

Signed and Sealed this

Thirty-first Day of March, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,144,721 B1
APPLICATION NO. : 10/111252
DATED : December 5, 2006
INVENTOR(S) : David I. Pritchard et al.

It is certified that error appears in the above-identified patent and that said Letters Patent is hereby corrected as shown below:

Title Page, Item (54) and Column 1, line 1,

In the Title:

The Patentee respectfully requests that the title on the cover page of the patent be changed from "The Treatment of Wounds" to "Lucilia *sericata* Serine Proteinase".

Item (73), In the Assignment:

The Assignee should be listed as "The Secretary of State for Defence", Defence Science and Technology Laboratory of Porton Down, Salisbury, Wiltshire, United Kingdom, SP4 0JQ (as correctly shown on the Assignment recorded in the United States Patent and Trademark Office on September 28, 2004).

In the Specification:

At column 1, line 29, "streptodomase" should read -- streptodornase --.

At column 1, line 56, "trysin" should read -- trypsin --.

At column 2, line 9, " insect" should read -- insects -- .

At column 2, line 21, "mammal" should read -- mammal, --.

At column 2, line 39, "mammal" should read -- mammal, --.

At Description of Figure 1, "(ES) having" should read -- (ES) secretions having --.

At column 3, line 36, "aminoacids" should read -- amino acids --.

At column 3, line 38, "peptides Leucine" should read -- peptides. Leucine --.

At column 4, line 13, "extra cellular" should read -- extra-cellular --.

At column 5, line 49, "was" should read -- were --.

At column 5, line 59, "a a" should read -- a --.

UNITED STATES PATENT AND TRADEMARK OFFICE
CERTIFICATE OF CORRECTION

PATENT NO. : 7,144,721 B1
APPLICATION NO. : 10/111252
DATED : December 5, 2006
INVENTOR(S) : David I. Pritchard et al.

It is certified that error appears in the above-identified patent and that said Letters Patent is hereby corrected as shown below:

At column 5, line 59, "chrymotrypsin-like" should read -- chymotrypsin-like --.

At column 6, line 36, "trysin-like" should read -- trypsin-like --.

In the Claims:

In column 9, line 29, "protcolytic" should read -- proteolytic - - .

In column 9, line 31, "protcolytic" should read -- proteolytic --.

In column 9, line 35, "AMPSF" should read -- APMSF --.

This certificate supersedes the Certificate of Correction issued March 31, 2009.

Signed and Sealed this

Twenty-first Day of April, 2009

JOHN DOLL
*Acting Director of the United States Patent and Trademark Office*

SEQUENCE LISTING

```
<160> NUMBER OF SEQ ID NOS: 5

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Phe Leu Leu Arg Asn
  1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Leu Ile Gly Lys Val
  1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Thr Phe Arg Gly Ala Pro
  1               5

<210> SEQ ID NO 4
<211> LENGTH: 6
<212> TYPE: PRT
<213> ORGANISM: Artificial Sequence
<220> FEATURE:
```

-continued

```
<223> OTHER INFORMATION: Description of Artificial Sequence: Synthetic
      peptide

<400> SEQUENCE: 4

Gly Tyr Pro Gly Gln Val
  1               5

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Suc-Ala

<400> SEQUENCE: 5

Ala Ala Pro Phe
  1
```